United States Patent [19]

Morse

[11] Patent Number: 5,795,324

[45] Date of Patent: Aug. 18, 1998

[54] WOUND AND LAVAGE IRRIGATION CAP APPARATUS AND METHOD FOR USING

[75] Inventor: Jeffrey W. Morse, Vacaville, Calif.

[73] Assignee: The United States of America as represented by the Secretary of the Air Force, Washington, D.C.

[21] Appl. No.: 368,261

[22] Filed: Dec. 27, 1994

[51] Int. Cl.$^6$ .................................................. A61M 1/00
[52] U.S. Cl. .................. 604/27; 604/257; 604/19; 604/28; 604/73
[58] Field of Search .................. 604/257, 19, 39, 604/36, 37, 27, 28, 54, 48, 73, 212, 262, 275, 279, 30, 150, 43; 222/92, 416, 460, 566, 567, 568; 215/316

[56] References Cited

U.S. PATENT DOCUMENTS

| | | | |
|---|---|---|---|
| 388,029 | 8/1888 | Dunn | 604/212 |
| 2,782,784 | 2/1957 | Ritter | 604/212 |
| 2,908,609 | 10/1959 | Aterno et al. | 604/54 |
| 3,308,998 | 3/1967 | Oppasser et al. | 604/212 |
| 3,486,503 | 12/1969 | Porter et al. | 604/275 |
| 3,802,435 | 4/1974 | Claasen | 604/275 |
| 4,421,505 | 12/1983 | Schwartz . | |
| 4,459,318 | 7/1984 | Hyons | 604/275 X |
| 4,769,003 | 9/1988 | Stamler . | |
| 4,941,873 | 7/1990 | Fischer | 604/54 |
| 4,991,777 | 2/1991 | Sato | 604/275 X |
| 5,120,304 | 6/1992 | Sasaki . | |
| 5,125,914 | 6/1992 | Bassin | 604/275 |
| 5,219,337 | 6/1993 | Takata et al. | 604/257 X |
| 5,248,071 | 9/1993 | Ray | 222/568 |
| 5,320,256 | 6/1994 | Wood . | |
| 5,380,275 | 1/1995 | Kensey et al. | 604/27 |

OTHER PUBLICATIONS

Chisholm et al., Comparison of a New Pressurized Saline Canister Versus Syringe Irrigation For Lacertation Cleaning in the Emergency Department, Annals of Emergency Medicine, vol. 21, No. 1, pp. 1364/80–1367/83, Nov., 1994.

Primary Examiner—Wynn Wood Coggins
Assistant Examiner—N. Kent Gring
Attorney, Agent, or Firm—Fredric L. Sinder; Thomas L. Kundert; Bobby D. Scearce

[57] ABSTRACT

A new apparatus and method for irrigating wounds and for performing gastric lavage utilizes a novel cap that has a threaded end sized to screw onto available plastic bottles of sterile irrigation fluid or saline and a nozzle end having the shape of a syringe tip. The threaded end of the cap is screwed onto the plastic bottle of irrigation fluid and an intravenous (IV) catheter attached to the nozzle end. The plastic bottle of irrigation fluid is held and squeezed to direct a stream of irrigation fluid through the IV catheter and into the wound. For gastric irrigation, a nasogastric tube is attached to the nozzle end and the bottle of irrigation fluid held and squeezed to force irrigation fluid into the stomach.

9 Claims, 1 Drawing Sheet

5,795,324

1

WOUND AND LAVAGE IRRIGATION CAP APPARATUS AND METHOD FOR USING

RIGHTS OF THE GOVERNMENT

The invention described herein may be manufactured and used by or for the Government of the United States for all governmental purposes without the payment of any royalty.

BACKGROUND OF THE INVENTION

The present invention relates generally to apparatus and methods for irrigating wounds and for performing gastric lavage, and more specifically to a cap for use with available plastic bottles of irrigation fluid that eliminates most of the parts and steps needed by the prior art.

A number of methods are used to irrigate wounds and to perform gastric lavage in a hospital setting. The most common method for wound irrigation, which is a key part of wound treatment and preventing infection, is to pour sterile irrigation fluid, generally a saline solution, into a sterile bowl, draw the fluid up aseptically a number of times into a sterile syringe, aseptically attach a sterile 18 or 20 gauge intravenous ("IV") catheter and then squirt the fluid into the wound under pressure to wash away gross contamination and to reduce the number of bacteria in the wound area. The IV catheter, a short plastic tube which typically surrounds an IV needle and remains in place as the opening into a vein after the IV needle is removed, fits over the end of a syringe the same as a needle, but provides a blunt plastic opening which is safer for irrigation than a sharp needle. This method requires sterile prepackaged irrigation fluid or saline, a sterile prepackaged bowl, a sterile prepackaged syringe, a sterile prepackaged IV catheter and a number of repetitive steps. The process is both time-consuming and costly. Not only is there the cost of all the sterile components (which includes the labor and time for sterilizing and packaging the components), but also the cost for the time required to repeatedly (depending on the size of the wound) draw up and squirt 20–50 cc's of sterile irrigation fluid. Most irrigations require several 20–50 cc incremental irrigations.

The most common method for gastric lavage, commonly called stomach pumping, requires a nasogastric tube (a long, flexible, sterile plastic tube), a supply of irrigation fluid and an irrigation syringe. The nasogastric tube is passed through the nares, or nostril passages, and swallowed into the stomach. The other end of the tube is temporarily taped in place under the nose and irrigation fluid pushed with the irrigation syringe through one of the tube passageways and into the stomach. The fluid is next removed by attaching the same tube passageway to suction and the removed fluid evaluated for diagnostic purposes. If deleterious material is found, such as blood or overdose pill fragments, the process can be repeated until as much of the deleterious material as possible is removed.

One alternative to the conventional manual method for wound irrigation is to use an IRRIJET brand wound irrigation apparatus, a self-filling, continuous syringe-based irrigation apparatus attached to a reservoir bag of sterile saline and intended for use with multiple patients. Although this apparatus was initially enthusiastically embraced in emergency departments, over time the combination of high cost and the time required for nursing staff to set up the apparatus has often resulted in a return to older manual methods, even in emergency rooms with access to an IRRIJET brand apparatus.

Another alternative to the conventional manual method for wound irrigation is to use a DEY-WASH brand wound irrigation apparatus, a single-use, pressurized, disposable canister of aseptically packaged sterile saline. Pressurized canisters introduce an environmental disposal problem. Each DEY-WASH brand canister is fairly expensive and contains only about 250 cc of saline solution, about enough to irrigate a single one inch laceration.

A further alternative to the conventional manual method for wound irrigation is to attach a sterile IV catheter to one end of a sterile IV tube, attach the other end of the IV tube to a sterile IV fluid bag, then either gravity flow the IV fluid through the tube into the wound or place a blood pressure cuff, or the like, around the IV bag and intermittently blow up the blood pressure cuff to generate a pressure head at the end of the catheter to irrigate the wound. This method requires considerable sterile equipment, is time consuming and labor intensive and, due to flow resistance from its length and the relative narrowness of its opening, the IV tubing creates a pressure loss that makes it difficult to generate a pressure head at the end of the tubing adequate to irrigate a wound. The literature suggests a 7–8 psig irrigation pressure is needed to adequately irrigate a deep, contaminated wound. It is difficult to attain this pressure with IV tubing.

Unfortunately, despite these and other prior art attempts to improve on the manual method for wound irrigation, none of them has been sufficiently successful to replace the manual method, with all its costs and delays, as the method of choice in most hospital settings. The same is true for prior art attempts to improve on methods for pushing irrigation fluid through a nasogastric tube. The primary problem of prior art solutions is that in attempting to improve on and simplify conventional methods, they add their own unwelcome complexity.

Thus it is seen that there is still a need for apparatus and methods for simplifying conventional wound and lavage irrigation procedures.

It is, therefore, a principal object of the present invention to provide a cap for use with available bottles of sterile irrigation fluid or saline that eliminates many of the parts and steps needed by the prior art for wound and lavage irrigation.

It is a feature of the present invention that it not only uses fewer parts, and is less expensive, than the prior art, but also reduces the amount of time necessary to set up and perform wound and lavage irrigation.

It is another feature of the present invention that it is particularly easy to use, its use being intuitive.

It is a further feature of the present invention that it makes it easy to vary an irrigation stream between light or forceful and between thin or wide.

It is an advantage of the present invention that it makes a more compact irrigation apparatus than prior art manual methods.

It is another advantage of the present invention that it is particularly suited for use away from hospitals, such as at battlefields and in the wilderness.

These and other objects, features and advantages of the present invention will become apparent as the description of certain representative embodiments proceeds.

SUMMARY OF THE INVENTION

The present invention provides a new cap for use with available plastic bottles of sterile irrigation fluid, and a related method, that significantly reduces the number of parts and steps needed for irrigating wounds and for performing gastric lavage. The breakthrough discovery of the present invention is that most of the parts and steps needed for prior art wound and lavage irrigation can be eliminated by replacing myriad apparatus with a single cap having a threaded end for screwing onto available plastic bottles of sterile irrigation fluid or saline and a nozzle end having the shape of a syringe tip. For wound irrigation, the threaded end is simply screwed onto a plastic bottle of irrigation fluid or saline and an IV catheter attached to the nozzle end in the same manner as to a syringe. Pressure is applied to the bottle and the resulting stream of irrigation fluid from the IV catheter used to irrigate the wound. For gastric lavage, the nozzle end includes a plurality of annular ridges for securing a nasogastric tube to the nozzle end. All of these steps can be performed quickly and easily.

Accordingly, the present invention is directed to a cap for use in wound and lavage irrigation, comprising a threaded end for screwing onto a bottle of sterile irrigation fluid and a nozzle end having the shape of a syringe tip. The cap may also include on the nozzle end a plurality of annular ridges for securing a tube onto the nozzle end.

The present invention is also directed to an apparatus for wound irrigation, comprising a plastic bottle of sterile irrigation fluid, the plastic bottle having a threaded opening, and, a cap having a threaded end for screwing onto the bottle of sterile irrigation fluid and a nozzle end having the approximate shape of a syringe tip. The apparatus may also include an IV catheter attached to the nozzle end of the cap.

The present invention is further directed to an apparatus for gastric irrigation of a stomach, comprising a plastic bottle of sterile irrigation fluid, the plastic bottle having a threaded opening, a cap having a threaded end for screwing onto the bottle of sterile irrigation fluid and a nozzle end having the shape of a syringe tip, the nozzle end including a plurality of annular ridges, and a nasogastric tube attached to the nozzle end of the cap.

The present invention is still further directed to a method for performing irrigation of a wound, comprising the steps of providing a plastic bottle of sterile irrigation fluid, the plastic bottle having a threaded opening, providing a cap having a threaded end for screwing onto the threaded opening of the plastic bottle of sterile irrigation fluid and a nozzle end having the approximate shape of a syringe tip, screwing the threaded end of the cap onto the threaded opening of the plastic bottle, next squeezing the plastic bottle, and next directing the resulting stream of irrigation fluid from the nozzle end of the cap into the wound to irrigate the wound. The method may also include the steps of providing an IV catheter and attaching the IV catheter to the nozzle end of the cap before squeezing the plastic bottle.

The present invention is yet further directed to a method for performing gastric irrigation of a stomach, comprising the steps of providing a plastic bottle of sterile irrigation fluid, the plastic bottle having a threaded opening, providing a nasogastric tube, providing a cap having a threaded end for screwing onto the threaded opening of the plastic bottle of sterile irrigation fluid and a nozzle end having the approximate shape of a syringe tip, the nozzle end including a plurality of annular ridges for securing a tube onto the nozzle end, screwing the threaded end of the cap onto the threaded opening of the plastic bottle, attaching the nasogastric tube over the annular ridges of the nozzle end of the cap, next passing the nasogastric tube into the stomach, and next squeezing the plastic bottle to force irrigation fluid through the nasogastric tube and into the stomach.

DESCRIPTION OF THE DRAWINGS

The present invention will be more clearly understood from a reading of the following detailed description in conjunction with the accompanying drawings wherein.

DETAILED DESCRIPTION

Figure 1:
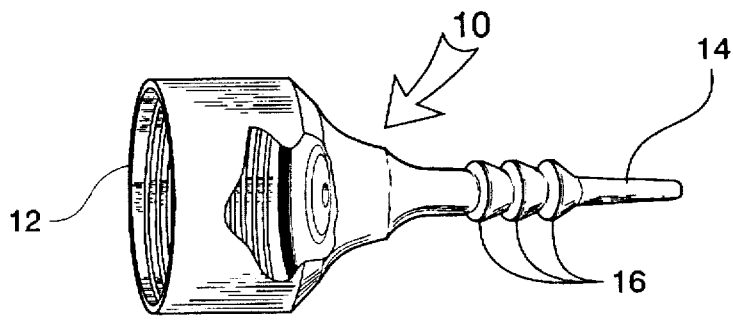
FIG. 1 is a perspective view of a wound and lavage irrigation cap made according to the teachings of the present invention showing its threaded end and its nozzle end.

Referring now to FIG. 1 of the drawings, there is shown a perspective view of a wound and lavage irrigation cap 10 made according to the teachings of the present invention. Cap 10 includes a threaded end 12 sized to screw onto available plastic bottles of sterile irrigation fluid or saline and a nozzle end 14 shaped the same as a conventional IV syringe, so that a conventional IV needle or IV catheter will friction fit onto nozzle end 14 the same as on an IV syringe. Nozzle end 14 also includes annular ridges 16 for better securing of nasogastric tubing that might be attached to nozzle 14. Annular ridges 16 are shown slightly backwardly slanted to provide a better grip for a hose or tube. Cap 10 also includes an interior rubber gasket, not shown, to improve sealing.

Figure 2:
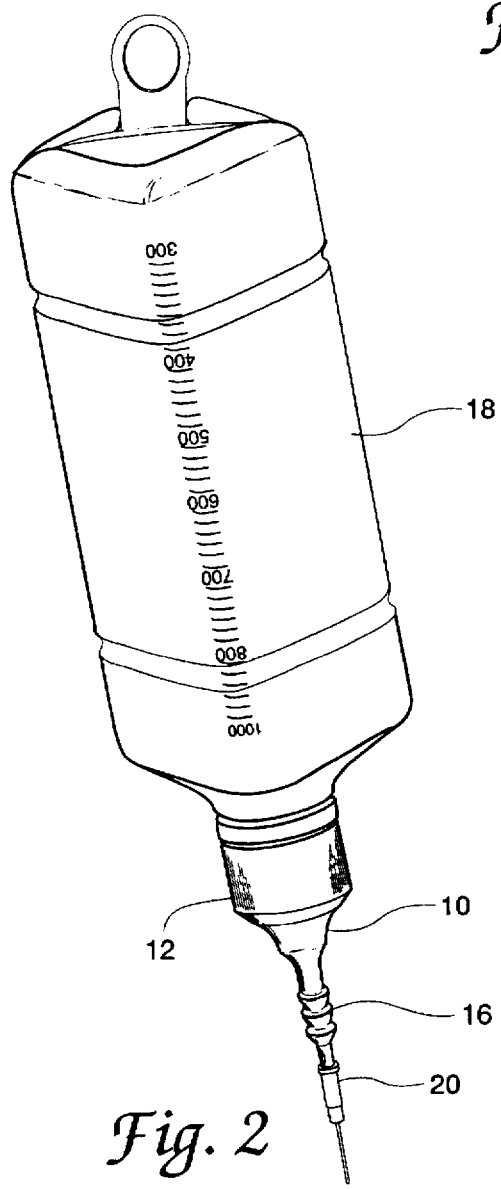
FIG. 2 is a perspective view of the wound and lavage irrigation cap of FIG. 1 showing its attachment to a plastic bottle of irrigation fluid or saline and an IV catheter attached to its nozzle end for use in wound irrigation; and, FIG. 3 is a perspective view of the wound and lavage irrigation cap of FIG. 1 showing its attachment to a bottle of irrigation fluid or saline and a nasogastric tube attached to its nozzle end for gastric irrigation.

FIG. 2 is a perspective view of wound and lavage irrigation cap 10 showing its attachment to a plastic bottle 18 of sterile irrigation fluid or saline and an IV catheter 20 attached to its nozzle end 14 for use in wound irrigation. Plastic bottle 18 is a conventional item typically prepackaged and filled with either sterile saline fluid or sterile water. Bottle 18 is available in several sizes, holding 250 ml, 500 ml or 1000 ml quantities of fluid. Nearly any sterile saline solution will be suitable for wound irrigation. In the future, depending on cost and convenience, conventionally available bottles 18 can be used or the market may supply similar bottles with a sterile saline solution designed more specifically for wound irrigation.

To use cap 10 for wound irrigation, threaded end 12 is aseptically screwed onto plastic bottle 18, as shown in FIG. 2, and IV catheter 20 slipped over nozzle end 14. The size, or gauge, of IV catheter 20 is chosen according to amount of stream pressure and width required. To irrigate a wound, plastic bottle 18 is held and squeezed, and catheter 20 pointed, to direct a stream of irrigation liquid into the wound. An IV catheter is not required for wound irrigation, but improves the process by more accurately directing the stream of irrigation fluid. That nozzle end 14 has the shape of an IV syringe also allows the attachment of other devices designed for use with syringes, such as splashshields.

Figure 3:
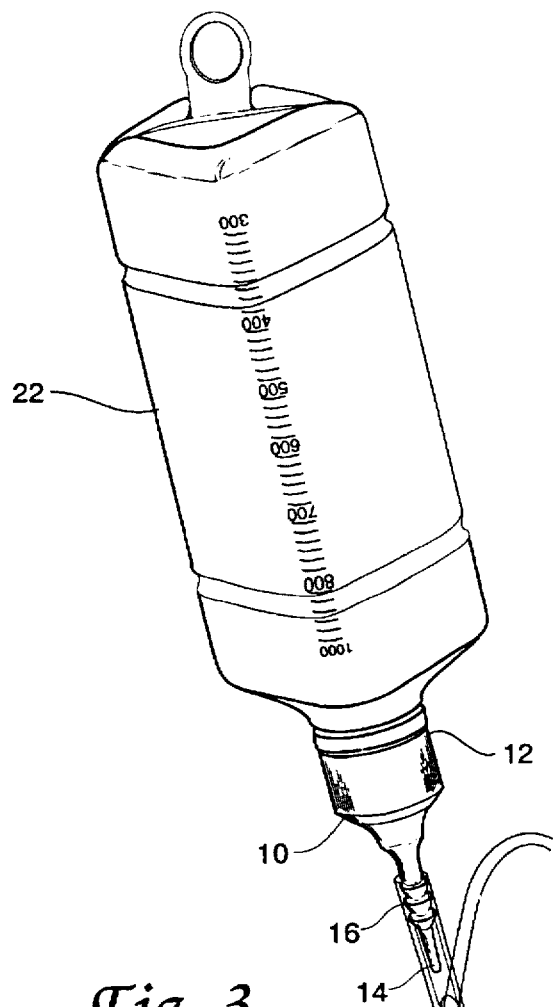

FIG. 3 is a perspective view of wound and lavage irrigation cap 10 showing its attachment to a bottle of irrigation fluid 22 or saline and a nasogastric tube 24 attached to its nozzle end for gastric irrigation. To use cap 10 for gastric irrigation, threaded end 12 is aseptically screwed onto plastic bottle 22, nasogastric tube 24 slipped over the annular ridges of nozzle end 14 and tube 24 inserted through the nares into the stomach. After taping nasogastric tube 24 in place under the nose, bottle 22 is squeezed to push gastric irrigation fluid into the stomach.

The order in which the various connection steps for performing wound irrigation and gastric lavage are performed is not critical.

Cap 10 is preferably made of injection-molded plastic, but may be made of any suitable material. Cap 10 will be sterilized by conventional methods and packaged inside a sterile plastic bubble. Cap 10 will usually be about 7 cm long, with a maximum outside middle diameter of about 4.3 cm, having an inside threaded diameter of about 3.8 cm on its threaded end and tapering on its nozzle end to a minimum outside diameter of about 4 mm and inside diameter of about 2 mm.

The described invention makes wound irrigation easier in circumstances and locations less well-equipped than, for example, a hospital emergency room. For example, for use with specialty medical kits such as are often used for the battlefield and even for camping trips, an empty plastic bottle, a salt tablet and a cap according to the teachings of the present invention provide a convenient wound irrigation kit. To use, the water is boiled or filtered with commercially available portable apparatus, poured into the plastic bottle, a salt tablet added, the cap screwed on and the wound irrigated as previously described.

The disclosed cap for use in wound and lavage irrigation successfully demonstrates the advantages of replacing an intricate to assemble multiplicity of separate components with a single, specially designed cap. The substitution of a single cap not only simplifies the assembly of an irrigation apparatus, but synergistically makes it easier to use. Although the disclosed cap is specialized, its teachings will find application in other areas where multiple parts may be advantageously combined into one part.

Modifications to the invention as described may be made, as might occur to one with skill in the field of the invention, within the intended scope of the claims. Therefore, all embodiments contemplated have not been shown in complete detail. For example, the term "squeezing," as used in the claims, seemingly implies manually compressing the bottle to force out a stream of sterile irrigation fluid, although a machine driven mechanism or a blood pressure cuff for compressing the bottle could be substituted within the scope of the claims. Similarly, other embodiments may be developed without departing from the spirit of the invention or from the scope of the claims.

I claim:

1. A cap for use in wound and lavage irrigation, comprising, on one end of the cap, a threaded end for screwing onto a bottle of sterile irrigation fluid and, on the other end of the cap, a nozzle end having the size and shape of a syringe tip.

2. The cap for use in wound and lavage irrigation according to claim 1, further comprising on the nozzle end a plurality of annular ridges for securing a tube onto the nozzle end.

3. A cap for use in wound and lavage irrigation, comprising, on one end of the cap, a threaded end for screwing onto a bottle of sterile irrigation fluid and, on the other end of the cap, a nozzle end having the size and shape of a syringe tip, the nozzle end including a plurality of annular ridges for securing a tube onto the nozzle end.

4. An apparatus for wound irrigation, comprising:
   (a) a plastic bottle of sterile irrigation fluid, the plastic bottle having a threaded opening; and,
   (b) a cap having, on one end of the cap, a threaded end for screwing onto the bottle of sterile irrigation fluid and, on the other end of the cap, a nozzle end having the approximate size and shape of a syringe tip.

5. The wound irrigation apparatus according to claim 4, further comprising an IV catheter attached to the nozzle end of the cap.

6. An apparatus for gastric irrigation of a stomach, comprising:
   (a) a plastic bottle of sterile irrigation fluid, the plastic bottle having a threaded opening;
   (b) a cap having, on one end of the cap, a threaded end for screwing onto the bottle of sterile irrigation fluid and, on the other end of the cap, a nozzle end having the size and shape of a syringe tip, the nozzle end including a plurality of annular ridges; and,
   (c) a nasogastric tube attached to the nozzle end of the cap.

7. (amended) A method for performing irrigation of a wound, comprising the steps of:
   (a) providing a plastic bottle of sterile irrigation fluid, the plastic bottle having a threaded opening;
   (b) providing a cap having, on one end of the cap, a threaded end for screwing onto the threaded opening of the plastic bottle of sterile irrigation fluid and, on the other end of the cap, a nozzle end having the approximate size and shape of a syringe tip;
   (c) screwing the threaded end of the cap onto the threaded opening of the plastic bottle;
   (d) next squeezing the plastic bottle; and,
   (e) next directing the resulting stream of irrigation fluid from the nozzle end of the cap into the wound to irrigate the wound.

8. The method for performing irrigation of a wound according to claim 7, further comprising the steps of:
   (a) providing an IV catheter;
   (b) attaching the IV catheter to the nozzle end of the cap before squeezing the plastic bottle; and,
   (c) wherein step (e) is characterized as next directing the resulting stream of irrigation fluid from the IV catheter into the wound to irrigate the wound.

9. A method for performing gastric irrigation of a stomach, comprising the steps of:
   (a) providing a plastic bottle of sterile irrigation fluid, the plastic bottle having a threaded opening;
   (b) providing a nasogastric tube;
   (c) providing a cap having, on one end of the cap, a threaded end for screwing onto the threaded opening of the plastic bottle of sterile irrigation fluid and, on the other end of the cap, a nozzle end having the approximate size and shape of a syringe tip, the nozzle end including a plurality of annular ridges for securing a tube onto the nozzle end;
   (d) screwing the threaded end of the cap onto the threaded opening of the plastic bottle;
   (e) attaching the nasogastric tube over the annular ridges of the nozzle end of the cap;
   (f) next passing the nasogastric tube into the stomach; and,
   (g) next squeezing the plastic bottle to force irrigation fluid through the nasogastric tube and into the stomach.

* * * * *